United States Patent [19]
Allen

[11] Patent Number: 5,342,353
[45] Date of Patent: Aug. 30, 1994

[54] SYSTEM FOR LASER TREATMENT OF THE FEMALE URETHRA AND BLADDER

[76] Inventor: Paul M. Allen, P.O. Box 1345, Pascagoula, Miss. 39568

[21] Appl. No.: 879,954

[22] Filed: May 6, 1992

Related U.S. Application Data

[63] Continuation of Ser. No. 609,903, Nov. 5, 1990.

[51] Int. Cl.$^5$ .................................................. A61B 17/36
[52] U.S. Cl. ........................................ 606/14; 606/13; 128/7; 607/89
[58] Field of Search ............... 128/6, 7, 395, 396, 128/397, 398; 606/2, 13, 14; 604/21

[56] References Cited

U.S. PATENT DOCUMENTS

| | | | |
|---|---|---|---|
| 2,797,683 | 7/1957 | Aiken | 128/398 |
| 2,922,415 | 1/1960 | Campagna | 128/398 |
| 3,417,746 | 12/1968 | Moore et al. | 128/398 |
| 3,889,661 | 6/1975 | Fiore | 128/6 |
| 4,211,229 | 7/1980 | Wurster | 606/18 |
| 4,597,380 | 7/1986 | Raif et al. | 128/6 |

*Primary Examiner*—Peter A. Aschenbrenner
*Attorney, Agent, or Firm*—Pravel, Hewitt, Kimball & Krieger

[57] ABSTRACT

A CO2 laser system which includes the CO2 laser unit, a microscope for receiving the laser beam and directing the beam to the infected area; a modified air cystoscope which further comprises a first primary member having a shaft portion with a continuous bore therethrough; a flare neck portion, and a handle member attached to the flared neck member; a secondary member, further comprising a primary shaft portion and enlarged cone portion, and a rear handle portion, with the outer diameter of the cone being of substantially the same diameter as the inner diameter of the shaft member, so that upon being inserted into the shaft member the cone would protrude out from the shaft member and serve as a means for directing the shaft into the female urethra opening thus eliminating the blunt end of the shaft making contact therewith. There would further be included a means for removing the secondary member from the bore in the shaft, to expose the urethra wall or trigone area for visualization through the bore in the shaft, and means for further directing a laser beam through the opening in the shaft for making direct with the infected area either on the trigone or the wall of the urethra, depending on the area to be treated.

6 Claims, 5 Drawing Sheets

SYSTEM FOR LASER TREATMENT OF THE FEMALE URETHRA AND BLADDER

This is a continuation of copending application Ser. No. 07/609,903, filed Nov. 5, 1990.

BACKGROUND OF THE INVENTION

1. Field of the Invention

The apparatus of the present invention relates to laser surgery. More particularly, the present invention relates to an apparatus, or modified air cystoscope utilized in a system for the treatment of the female urethral and trigone portion of the bladder using the CO2 laser primarily for eradicating urethral and trigonal condylomata acuminata.

2. General Background

In the treatment of diseases concerning the female urethral and the floor of the bladder, or trigone, visualization of the infected areas has been undertaken by the use of an apparatus known as a Kelly Air Cystoscope. Such a device included a handle member attached to a hollow shaft portion which terminated in a flared neck to which the handle was attached. There is included a second portion comprising a primary shaft with a cone on the forward portion of the shaft, and a handle portion on the rear portion of the shaft, with the second member insertable into the bore of the shaft so that once fully inserted the cone portion would protrude out from the distal end of the shaft, and the handle portion could be grasped together with the handle portion at the primary member. The device was of a particular length and diameter so that it could be inserted into the urethra opening of the female bladder, and when the secondary portion was then removed from the shaft, one could visually inspect through the bore the trigone area of the bladder, or the wall of the urethra opening, in order to determine whether infections or the like are present in these areas. This tool was used primarily, but not exclusively, as a visualization tool, prior to treatment of these areas in the most common manner.

With the on-set of the use of laser treatment of infected areas, such as bladder or urethra infections, one of the more particular problems in the treatment of these areas with the laser, is the ability to direct the laser beam directly to the infected area so that the beam is not hindered in it's passage through the urethra opening. This problem is an on-going problem and was heretofore unsolved until the use of the combination of the laser beam with the modified cystoscope as heretofore as described, by the present inventor.

The prior art would disclose the Kelly Cystoscope in all of the classic literature in the area of urethra or trigone infections, and the Kelly Air Cystoscope is a known apparatus used widely over many years in the medical field. Further, there are patents which were found as a result of a search conducted in the U.S. Patent Office, which address the type of an apparatus which may be used in the similar manner as a Kelly Air Cystoscope, these patents which are as follows:

| PATENT NO. | PATENTEE | TITLE |
| --- | --- | --- |
| 2,279,714 | Meyerhof | "Cystoscope" |
| 2,487,498 | Wallace | "Cystoscope" |
| 4,211,229 | Wurster | "Laser Endoscope" |
| 4,266,548 | Davi | "Apparatus For And Method Of Utilizing Energy To Excise Pathological Tissue" |
| 4,313,431 | Frank | "Endoscopic Apparatus With A Laser Light Conductor" |
| 4,557,255 | Goodman | "Urethroscope" |
| 4,630,598 | Bonnet | "Uretero-Renoscope" |
| 4,760,840 | Fournier, Jr. | "Endoscopic Laser Instrument" |
| 4,881,524 | Boebel | "Instrument For Guiding A Laser Light Transmitting Fiber" |
| 4,899,734 | Gelley | "Speculum With Arresting Device" |

SUMMARY OF THE PRESENT INVENTION

The system of the present invention would solve the problems in the art in a simple and straightforward manner. What is provided is a CO2 laser system which includes the CO2 laser unit, a microscope for receiving the laser beam and directing the beam to the infected area; a modified air cystoscope which further comprises a first primary member having a shaft portion with a continuous bore therethrough; a flared neck portion, and a handle member attached to the flared neck member; a secondary member, further comprising a primary shaft portion and enlarged cone portion, and a rear handle portion, with the outer diameter of the cone being of substantially the same diameter as the inner diameter of the shaft member, so that upon being inserted into the bore of the primary member the cone would protrude out from the shaft member and serve as a means for directing the shaft into the female urethra opening thus eliminating the blunt end of the shaft making contact therewith. There would further be included a means for removing the secondary member from the bore in the shaft, to expose the urethral wall or trigone area of the bladder for visualization through the bore in the shaft, and means for further directing a laser beam through the opening in the shaft for making direct contact with the infected area either on the trigone or the wall of the urethra, depending on the area to be treated.

Therefore, it is a principal object of the present invention to provide a CO2 laser treatment system for treating the urethra or the trigone of a female bladder, with the use of a modified kelly air cystoscope in directing a laser beam thereunto;

It is a further object of the present invention to provide a modified kelly air cystoscope which enables a laser beam to be directed to the urethra or trigone area of the female bladder through the urethral opening and making contact only with the infected area; and It is a further object of the present invention to provide a modified kelly air cystoscope for visualization and treatment of the female urethra and trigone area of the bladder, by serving as a means for directing a laser beam to the infected area of those portions of the urethra or trigone area of the female bladder.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
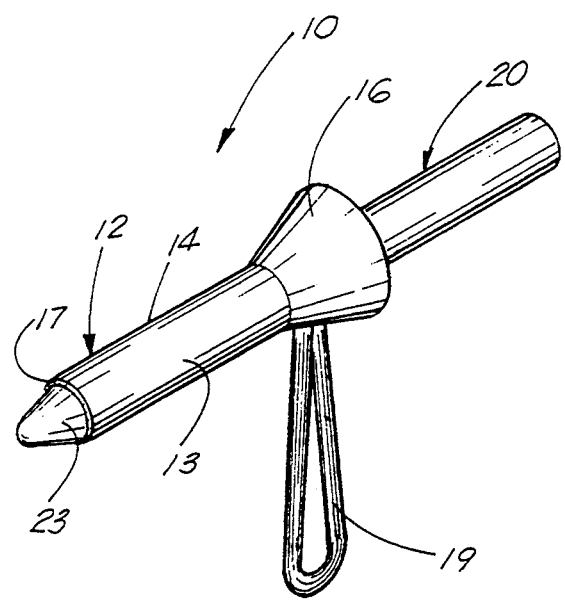
FIG. 1 illustrates an overall view of the modified cystoscope in the preferred embodiment of the present invention.
Figure 2:
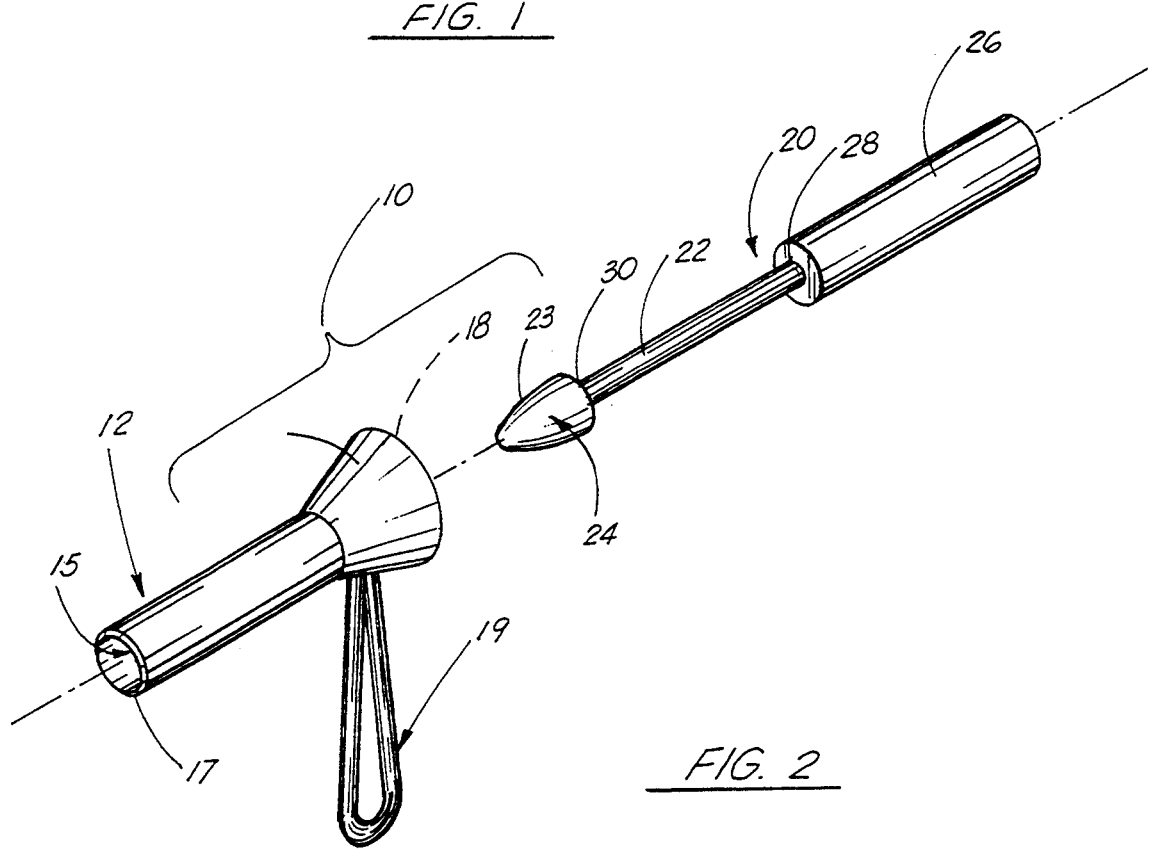
FIG. 2 illustrates an exploded view into the primary and secondary elements in the modified cystoscope utilized in the present invention.

The system of the present invention discloses a system for visualizing and treating through the use of a laser, such as a CO2 laser, an infected area of the female bladder, particularly the trigone area, or the wall of the female urethra. Utilized with that overall system, is a device which has been modified to be utilized in order to have the system achieve its success. The device which has been modified is a device which is widely known in the medical field as a Kelly Air Cystoscope, which has been used for many years, and was discussed earlier in the General Background of this application.

Following a discussion of the present invention it will be clearly shown that the modifications in the apparatus enable the apparatus to be utilized in the present system.

FIGS. 1 through 7 illustrate the preferred embodiment of the system of the present invention, with the modified air cystoscope being identified by the numeral 10. As illustrated, more clearly in FIGS. 1 and 2, cystoscope 10 comprises a primary member 12, and a secondary member 20. Primary member 12 includes a principal shaft portion 13 having a continuous annular wall 14, for defining a continuous bore 15 therethrough. Shaft member 13 would further include a flared annular neck portion 16, likewise having a flared bore 18 therethrough and in communication with the bore 15 of shaft portion 13. There would be further included a U-shaped handle member 19, preferably connectably engaged to the neck portion 16, with the handle portion 19 being substantially perpendicular to the length of the shaft portion so that as one would hold the handle portion 19, shaft portion 13 would be in the sight line between one sight and the area cited.

As further illustrated, secondary member 20 would comprise a reduced shaft portion 22, which would be solid shaft, having an enlarged cone member 24 on its forward end 30, and an extended columnar shaped handle portion 26 on its rear end 28, the length of distance between the rear face of cone 24 and the forward face of handle 26 would be of a distance substantially the length of shaft 13 of primary member 12, so that as the secondary member 20 is inserted into the bore 13 of shaft 12, the body portion 23 of cone member 24 would extend out of the distal end 17 of shaft 13 as illustrated in FIG. 1. When the entire modified cystoscope 10 has been assembled, as illustrated in FIG. 1, its assembly allows the easy maneuvering of the apparatus into the female urethral opening, with the cone 24 serving as a means for sliding the entire apparatus easily through the urethral opening without the blunt end 17 of shaft 13 making contact with the wall of the urethra opening which could cause discomfort to the patient.

In the present invention, the system of the present invention would utilize a wholly modified air cystoscope which has been modified in several critical configurations so that it can be utilized in the system in the present invention. As seen in FIG. 1, the length of the shaft of the primary member would be in the range between 2.5 and 5.0 centimeters which would make it very much of reduced length than the known Kelly Air Cystoscope. The width of the shaft would be in the range of 4 millimeters to 13.2 millimeters which would make it somewhat greater in diameter than the Kelly Air Cystoscope for the reasons that will be described further. Furthermore, the interior surface of the sheath wall would be treated or "brazed" so as to accommodate a laser beam therethrough without the beam causing increased glare should it make contact with the interior shaft wall.

Likewise, the secondary member of the Kelly Air Cystoscope would be of an overall length and diameter to enable it to be maneuvered into the shaft opening in the modified air cystoscope utilized in the present system.

In comparison, the original Kelly Air Cystoscope had the following dimensions: the primary member had a shaft length of approximately 10 centimeters, which would include the flared neck portion. The diameter of the shaft of the primary member is approximately 6.3 centimeters inside diameter, and the diameter of the flared neck portion is approximately 7.7 millimeters outside diameter, and the diameter of the flare neck portion is approximately 20.5 millimeters outside diameter and 18.5 millimeters inside diameter.

Reference will continue to be made to the configuration of the modified cystoscope utilized in the present invention so as to fully present its use and positioning prior to its being utilized with the other components of the system.

Figure 3:
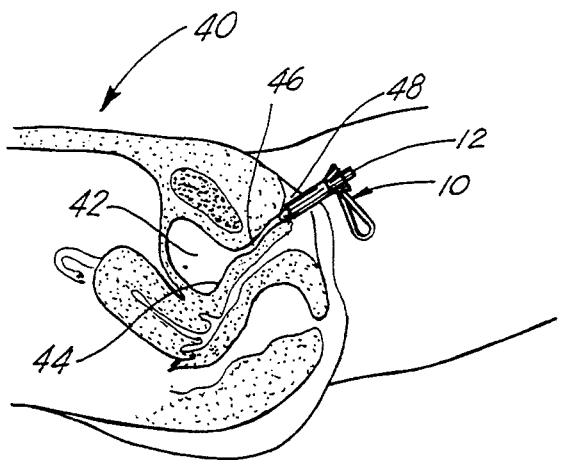
FIG. 3 illustrates an overall side view of the modified cystoscope being directed into the female urethra in the present invention.
Figure 6:
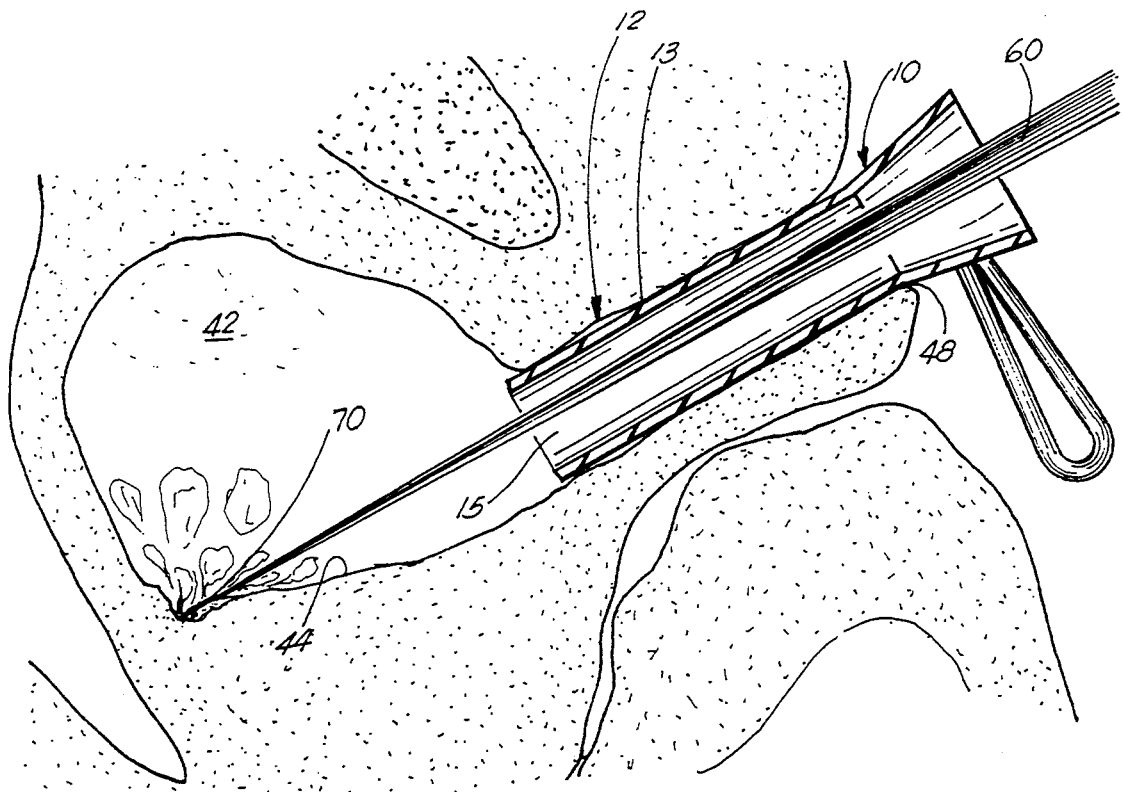
FIG. 6 is illustrates a detailed cross-sectional view of the laser being directed through the cystoscope to treat the trigone area of the bladder.

As illustrated in FIG. 3, in cross-section there is illustrated a female patient 40 set in the prone position, which, in cross-sectional view there is illustrated the bladder portion 42, with the trigone or floor of the bladder 44 and the urethral canal 46 extending from the exterior of the patient and leading into the bladder 42. As illustrated, apparatus 10, with the secondary member inserted in position, is being inserted into the outer opening 48 of the urethra, and will be slowly fully inserted into the urethra, with the cone portion 23 serving as a means to reduce the discomfort of positioning the apparatus fully into the urethra as it is seen in FIG. 3.

Figure 4:
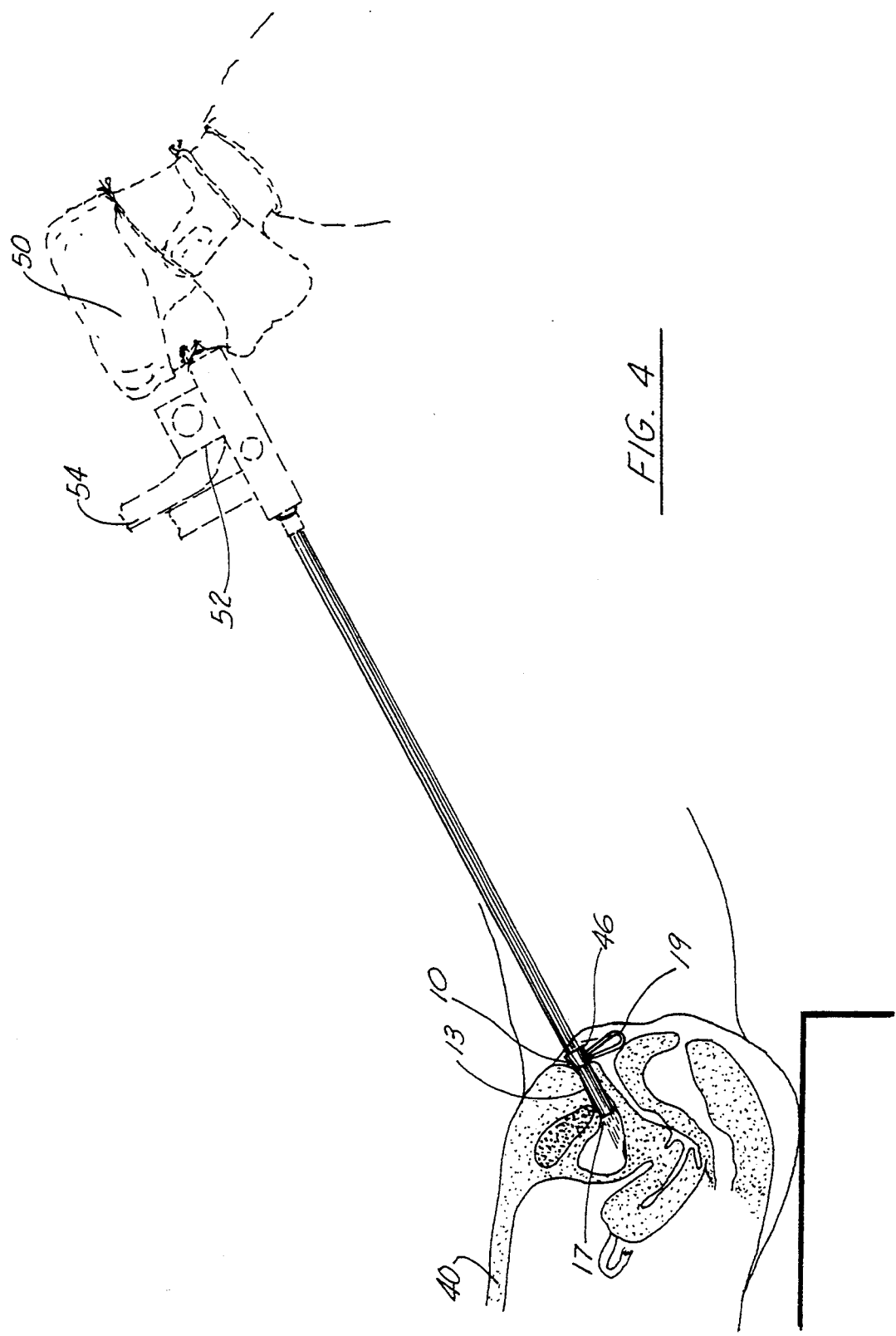
FIG. 4 illustrates an overall side view of the system of the present invention with the cystoscope fully inserted into the urethra opening, and the infected area being visualized therethrough.

As seen in FIG. 4, upon being fully inserted, the secondary member 12 has been then withdrawn from the opening in the shaft so that the primary member is maintained in place to be used in the system of the present invention.

Once in position, reference is made to FIG. 4, where there is illustrated the components of the system being utilized in visualization and subsequent treatment of the urethra and trigone area of the bladder. As illustrated, there is seen a medical doctor 50 viewing into a visualization apparatus such as a microscope 52, with the microscope so adapted as to receive a laser through portion 54, from a source not illustrated. Further in FIG. 4, modified cystoscope 10 is positioned in the urethra 46 with the distal end extending into the female bladder as illustrated. In this particular figure, the doctor is simply undergoing visual inspection of the bladder or urethra pathway in order to detect what areas are needed for CO2 laser treatment.

Figure 5:
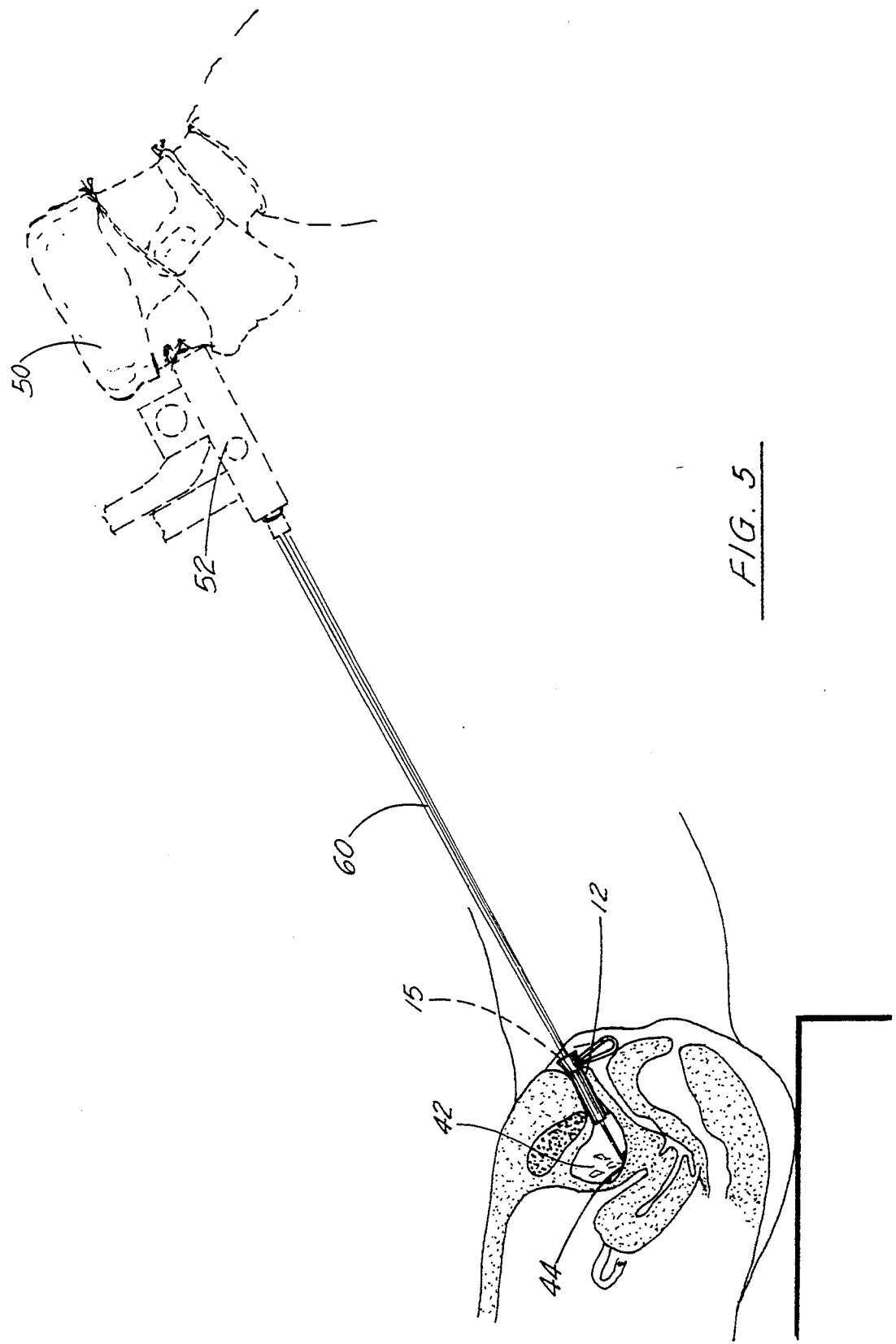
FIG. 5 illustrates an overall view of the system of the present invention with the laser being directed through the cystoscope to the infected area.

In FIG. 5, after the portion of the trigone area 44 has been clearly identified as needing treatment, doctor 50 has directed a CO2 laser beam as illustrated by line 60 through the viewing scope 52 and through the continuous bore 15 of the primary member 12, with the opening serving as a passageway directing laser beam 60 into the bladder 42 and making contact with the infected area of the trigone 44. It is through this combination of the cystoscope shaft member 12, and the critical length in allowing the shaft member to be fully inserted into the bladder 42 yet not be of such a length to obstruct the clear passageway of the beam 60 into the bladder 42 that the modified cystoscope 10 serves as a critical portion of the overall combination of the present invention.

Figure 7:
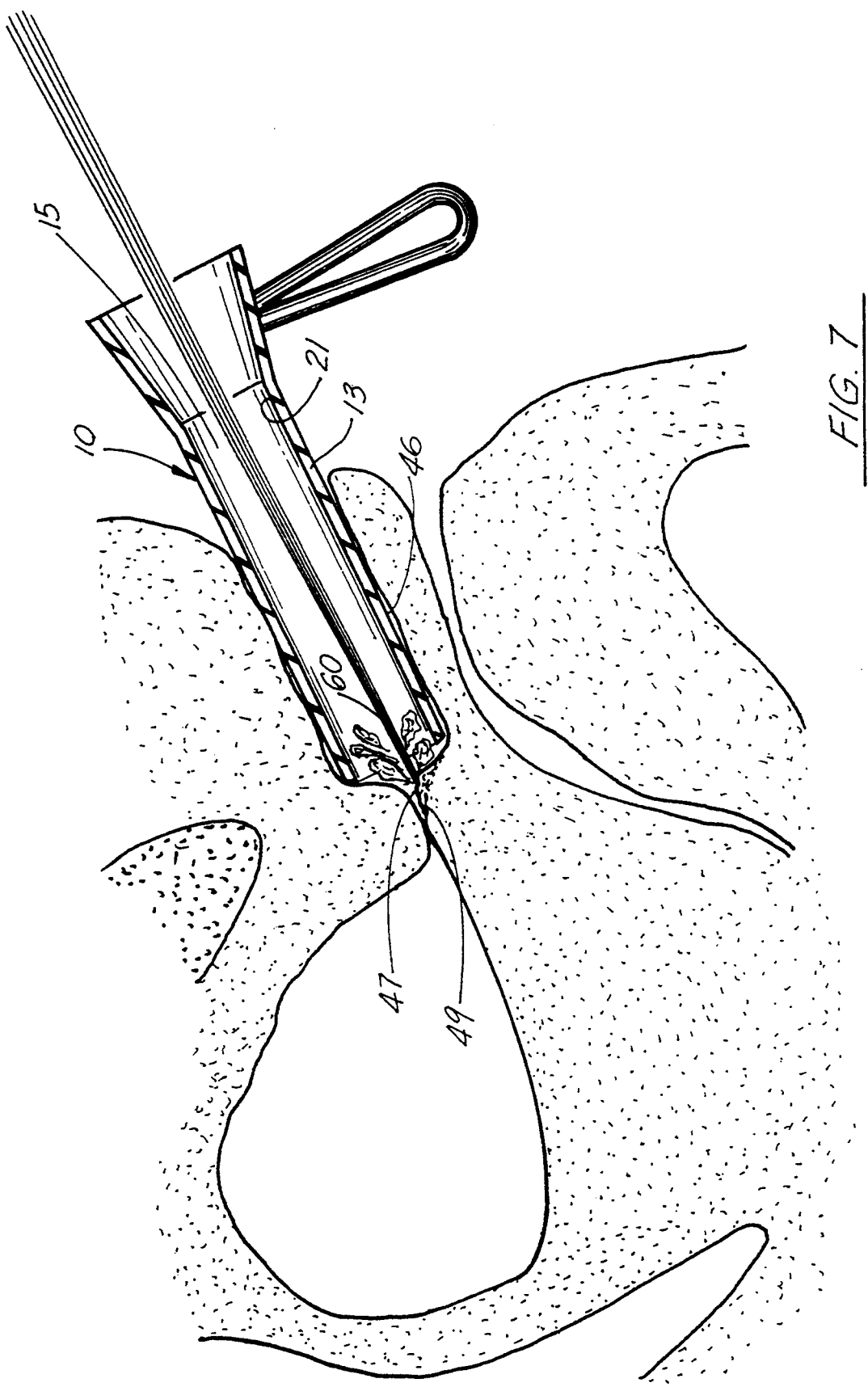
FIG. 7 illustrates the use of the cystoscope in the system of the present invention used to treat the urethra wall.

FIG. 6 again illustrates a detailed view of the cystoscope 10, as stated earlier fully inserted into the urethral opening 48 of the bladder 42, the laser beam 60 directed through the bore 15 in the shaft 13 of the primary member 12 of the cystoscope, and making contact with the infected area 70 in the trigone 44 of the bladder 42. FIG. 7 simply illustrates the use of the modified cystoscope member 10 as it would be used in the system in treating the wall of the urethra 46, in that the cystoscope shaft 13 is slowly backed out of the urethra and the wall 47 of the urethra is visually inspected and when the visual inspection would detect an infected point on the wall, the laser beam 60 could then be again directed through the bore 15 in the shaft 13 of the primary member 12, and directed to the infected point 49 on the wall of the urethra rather than to the trigone area.

As was stated earlier, the modified cystoscope 10 would allow clear passage of a CO2 laser beam 60 through the bore 15 of the shaft 12 either into the bladder 42 itself or to make contact with the wall 47 of the urethra 46, and the interior surface of the wall 13 of the shaft would further include a treated surface that has been brazed or dulled slightly, so that should the CO2 laser beam inadvertently make contact with the wall of the shaft, that the beam would not be deflected as would one be in a normally treated cystoscope shaft, but would continue in its pathway to treat the infected area.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A kit for conducting laser treatment of the female urethra and bladder, the kit comprising:
   a) a source for producing a laser beam;
   b) an operating microscope comprising a lens portion for magnifying the area to be viewed and a means for receiving and focusing the laser beam from the laser beam source into the area of the bladder or urethra to be treated;
   c) a cystoscope member comprising a shaft portion having a continuous bore therethrough, at least a portion of the shaft insertable into the urethra of a patient, to define a single passage through the continuous bore for viewing the area to be treated, and to transmit the focused laser beam through the shaft bore to the area of the urethra or bladder to be treated; and
   d) means positioned on the interior wall of the shaft of the bore of the cystoscope for reducing refraction of the laser beam as it travels through the bore of the shaft;
   the laser beam source and the operating microscope including the lens portion for magnifying the area to be viewed and the means for receiving and focusing the laser beam from the laser beam source positioned at a remote location from the cystoscope during transmission of the focused laser beam to the area to be treated.

2. The kit in claim 1, wherein the laser beam comprises a CO2 laser.

3. The kit in claim 1, wherein the shaft of the cystoscope member would be preferably between 2.5 and 5.0 centimeters in length and 4 to 13.2 millimeters in diameter.

4. The kit in claim 1, wherein the means on the interior wall of the bore of the shaft for reducing refraction of the laser beam further comprises a non-polished surface.

5. A System of individual components for treating infections of the female urethra and trigone area of the bladder, the system comprising:
   a) a source for producing a laser beam;
   b) an operating microscope comprising a lens portion for enlarging the view of the area to be treated, and for receiving and focusing the laser beam upon the area;
   c) a cystoscope member comprising a shaft portion having a continuous bore therethrough, at least a portion of the shaft insertable into the urethra of a patient, to define a single passage through the continuous bore for viewing the area to be treated, and to transmit the focused laser beam bore to the area of the urethra or bladder to be treated; and
   d) the laser beam source and the operating microscope including the lens portion for magnifying the area to be viewed and the means for receiving and focusing the laser beam from the laser beam source positioned at a remote location from the cystoscope during transmission of the focused laser beam to the area to be treated; and
   e) means on the interior wall of the shaft bore for reducing the refraction of the laser beam as it travels through the shaft bore.

6. The system in claim 5, wherein the laser beam comprises a CO2 laser.

* * * * *

UNITED STATES PATENT AND TRADEMARK OFFICE
CERTIFICATE OF CORRECTION

PATENT NO. : 5,342,353
DATED : August 30, 1994
INVENTOR(S) : Paul M. Allen, et. al.

It is certified that error appears in the above-indentified patent and that said Letters Patent is hereby corrected as shown below:

Title page, item [75] Inventor: should read as follows, Paul M. Allen, P.O. Box 1345, Pascagoula, Miss. 39568; Gordon D. Davis, 6225 E. Lafayette, Phoenix, Ariz. 85251--.

Signed and Sealed this

First Day of August, 1995

Attest:

BRUCE LEHMAN

*Attesting Officer*  *Commissioner of Patents and Trademarks*